US006806963B1

United States Patent
Wälti et al.

(10) Patent No.: US 6,806,963 B1
(45) Date of Patent: Oct. 19, 2004

(54) METHOD AND DEVICE FOR MEASURING THE OPTICAL PROPERTIES OF AT LEAST TWO REGIONS LOCATED AT A DISTANCE FROM ONE ANOTHER IN A TRANSPARENT AND/OR DIFFUSE OBJECT

(75) Inventors: Rudolf Wälti, Liebefeld (CH); Gregor F. Schmid, Savièse (CH)

(73) Assignee: Haag-Streit AG, Koniz (CH)

(*) Notice: Subject to any disclaimer, the term of this patent is extended or adjusted under 35 U.S.C. 154(b) by 0 days.

(21) Appl. No.: 10/130,994

(22) PCT Filed: Nov. 24, 2000

(86) PCT No.: PCT/CH00/00634
§ 371 (c)(1),
(2), (4) Date: Jul. 23, 2002

(87) PCT Pub. No.: WO01/38820
PCT Pub. Date: May 31, 2001

(30) Foreign Application Priority Data

Nov. 24, 1999 (CH) ............................................ 2146/99

(51) Int. Cl.⁷ .................... G01B 11/02; G01B 11/00; G01B 9/02
(52) U.S. Cl. ................... 356/497; 356/359; 356/489; 356/495; 356/512
(58) Field of Search ................... 356/497, 359, 356/489, 495, 512

(56) References Cited

U.S. PATENT DOCUMENTS

| 4,534,649 | A | * | 8/1985 | Downs |
| 4,842,408 | A | * | 6/1989 | Yoshii et al. |
| 4,869,593 | A | * | 9/1989 | Biegen |
| 4,872,755 | A | * | 10/1989 | Kuchel |
| 5,033,855 | A | * | 7/1991 | Matsui |
| 5,488,477 | A | * | 1/1996 | de Groot |
| 5,671,050 | A | * | 9/1997 | de Groot |
| 5,923,425 | A | * | 7/1999 | Dewa et al. |
| 6,215,556 | B1 | * | 4/2001 | Zhang et al. |
| 6,359,692 | B1 | * | 3/2002 | Groot |

FOREIGN PATENT DOCUMENTS

| EP | 0 671 601 A2 | 9/1995 |
| EP | 0 932 021 A1 | 7/1999 |
| WO | 99/22198 A1 | 5/1999 |
| WO | 96/35100 A1 | 11/2000 |

* cited by examiner

Primary Examiner—Frank G. Font
Assistant Examiner—Khaled Brown
(74) Attorney, Agent, or Firm—Birch, Stewart, Kolasch & Birch, LLP (57) ABSTRACT

An optical arrangement of the Michelson interferometer type having a measuring arm for measuring optical properties of at least two mutually spaced regions in an optically transparent and/or diffusive object. A reference arm has a path length variation unit which generates a periodic change in path length for the radiation in the reference arm. Arranged in the measuring arm upstream of the object is a detour unit. The detour unit imparts a detour which is larger than at least one second measuring beam into at least one measuring beam. The detour unit selects a detour to be equal to a distance between regions to be measured in the object. Using the optical arrangement the object is irradiated with the aid of a number of measuring beams corresponding to the number of regions. In each case two measuring beams have an optical path difference which corresponds to a geometrical distance between two regions. Each reflection beam of the measuring beams which is reflected by one of the regions is superimposed in an interfering fashion with a third beam having a temporal variation in path length, and is detected. This arrangement can carry out "in-vivo" measurements of distances, thicknesses, at and/or in the human eye with the minimization of measuring errors within a sub-second time. The object does not have to be fixed during the measurement.

23 Claims, 7 Drawing Sheets

$\Delta = d_2 - d_1$

METHOD AND DEVICE FOR MEASURING THE OPTICAL PROPERTIES OF AT LEAST TWO REGIONS LOCATED AT A DISTANCE FROM ONE ANOTHER IN A TRANSPARENT AND/OR DIFFUSE OBJECT

This application is the national phase under 35 U.S.C. § 371 of PCT International Application No. PCT/CH00/00634 which has an International filing date of Nov. 24, 2000, which designated the United States of America.

TECHNICAL FIELD

The invention relates to a method, a device for measuring optical properties of at least two mutually spaced regions in the case of a transparent and/or diffusive object, and to their use for thickness, distance and/or profile measurement undertaken by means of short coherence reflectometry.

The transparency of objects is a function of their wavelength-dependent attenuation coefficient $\alpha$ [cm$^{-1}$] and their thickness as well as the prescribed measuring distance d. Objects noted as transparent are those whose transmission factor $T=\exp(-\alpha \cdot d)$ still lies within the measuring range of the interferometers described below, the transmission being $T^2$ in the interferometers described below because of the "round-trip path" of the radiation. In diffusive objects, the radiation is strongly scattered but not necessary absorbed. Milk glass plates, Delrin, organic tissue (skin, human and animal organs, plant parts etc.), for example, are to be regarded as diffusive objects.

Short coherence reflectometry has been used as a rule for precise, quick and non-invasive images. It has been typical for the beam of a radiation source to be split with a beam splitter in an optical arrangement with a Michelson interferometer into a reference and a measuring beam. As a rule, a radiation source with a short coherence length has been selected. Splitting into reference and measuring beam and reuniting them have been performed with a beam splitter and when fiberoptic paths are used with a fiber coupler. It has been possible to achieve the change in the optical path length in the reference arm by displacing a reference mirror on a translation stage. However, use has advantageously been made of a rotating transparent cube such as described in WO 96/35100. It is only when the path length difference is smaller than the coherence length of the radiation of the radiation source that the reflected reference and measuring beams have been recombined to form an interference pattern. The interference pattern has been brought onto a photodetector which has measured the intensity of radiation during the variation in the mirror position. Since the frequency of the radiation of the reflected reference beam has experienced a double shift owing to the mirror displacement, it has been possible for the interference signal to be evaluated with electronic means, as described in WO 99/22198, for example, by increasing the signal-to-noise ratio.

However, measuring errors have occurred when distances which have necessitated at least two measuring operations were to be measured in optically transparent objects, or objects transmitting an optical radiation diffusively, and the objects could be fixed within the required measuring tolerance over the entire measuring cycle only with difficulty or not adequately. These problems have arisen, in particular, in the case of in-vivo measurements.

SUMMARY OF THE INVENTION

Object of the invention

It is an object of the invention to present a method and to create a device with the aid of which method and/or device it is possible, in particular, to carry out optimally, that is to say with the minimization of measuring errors, in the case of in-vivo measurements of distances, thicknesses, surface profiles, which include measurements at different locations in an object.

Achievement of the object

The object is achieved by virtue of the fact that in order to measure optical properties using a measuring time in the subsecond range (necessary for an in-vivo measurement) of at least two mutually spaced regions in the case of a transparent and/or diffusive object, as necessary for measuring distance, length, thickness and profile, the object is irradiated simultaneously or in rapid sequence, with the aid of a number of measuring beams corresponding to the number of regions. The expression "in the case of" an object is intended to express that the regions can be located at the locations in the object as well as on the object, for example laterally offset. In each case two measuring beams have, except for a mutual determination tolerance, an optical path difference, that is to say a transit time difference. The transit time difference corresponds to an optical distance between two points in space (regions) with reference to the direction of propagation of the measuring radiation, at least one of the points in space being reflected at least slightly (typically at least $10^{-4}\%$ of the intensity of radiation). The measuring beams can thus be situated one above another (thickness, distance, length measurement), and parallel to one another (surface profile, . . . ) or exhibit any desired angle to one another (thickness, distance measurement, . . . in the case of a given angle to a reference surface). Each reflection beam of the measuring beams which is reflected by one of the regions is detected by superimposing on it in an interfering fashion a third beam having a temporal, preferably periodic, variation in path length.

After the path difference or differences has/have been taken, the measuring beams are combined, preferably for thickness measurement, to form a single beam configuration with a single optical axis. Again, the beam configuration can be moved, in particular periodically, over the object. This gives rise to lateral scanning. In conjunction with storage of the values determined, this scanning can lead to the creation of profiles. Instead of the two measuring beams being focused on an optical axis, however, it is also possible in each case for at least two measuring beams to run and be focused at a distance next to one another in order to determine a surface profile.

By comparison with the distances between regions, in particular with the distances between regions starting from a reference location, the measuring beams have a short coherence length. The measuring beams can, furthermore, in each case have mutually differing radiation frequencies. However, it is then necessary to use a plurality of radiation sources. It is also possible to work with only one radiation source and perform splitting via filters. However, this results in a loss of broadband capability; again, some of the components must be provided with an expensive coating.

Instead of different radiation frequencies, or as a supplement to this, the measuring beams can have mutually differing polarization states, which yields a simpler design. Focusing the measuring beams in the region or regions to be measured will also preferably be undertaken. Since the operation is carried out with an optical arrangement of the Michelson interferometer type, the instantaneous position of the reflecting element in the reference arm can serve as reference location. It is now possible for this purpose to use the actual position or another value coupled to the reference location such as, for example, the rotary position of the rotating cube described in WO 96/35100.

The measurement is carried out with an optical arrangement, of the Michelson interferometer type, into whose measuring arm the optically transparent and/or diffusive object can be introduced. Instead of an optically transparent and/or diffusive object, it is also possible to work with an object whose surface is reflecting, In the case of a reflecting object, it is possible to use the method according to the invention to determine its surface profile, in particular. However, the object can be optically transparent and/or diffusive, and have a surface which reflects (at least a few percent). It is then possible in this case to determine both surfaces and thicknesses and/or their profiles. The reference arm has a path length variation unit with the aid of which it is preferably possible to carry out a periodic change in path length in the reference arm. Arranged in the measuring arm upstream of the object is a detour unit with the aid of which at least one first measuring beam can be imparted a transit time which is longer than at least one second measuring beam, it being possible, except for a determination tolerance, to select a detour, which can be produced by the detour unit, to be equal to a distance between at least two regions to be measured in the object. In addition to regions (locations) for thickness measurement which are situated "one behind another" in the object, it is, of course, also possible to measure regions (locations) situated "next to one another" to determine surface curvatures and/or surface profiles.

The detour is set approximately in such a way that it corresponds to an expected measurement result of a thickness, distance, . . . to be determined, except for a determination tolerance. All that is then required is to use the path variation unit in the reference arm to determine the unknown fraction (to be determined) of the thickness, distance etc. If, for example, the actual length of a human eye is to be determined, it is, after all, known in advance that eyes have an optical length of 34 mm with a length tolerance of +/−4 mm. It is possible here to set a detour of 34 mm and to use the path variation unit to undertake a variation of only 8 mm.

In addition to the eye length, the device described below, and its design variants, can be used to measure the thickness of the cornea, the depth of the anterior chamber, the lens thickness and the depth of the vitreous humor, as well as corresponding surface profiles of the eye. For this purpose, the measuring beam specified for the surface of the eye as object surface is focused "somewhere" between the front of the cornea and the rear of the lens. It is then possible by means of this "compromise" to detect the reflection at the front of the cornea, the rear of the cornea, the front of the lens and the rear of the lens. The distance between the rear of the cornea and the front of the lens is then the depth of the anterior chamber. However, it is a condition for this measurement that the "optical" stroke (approximately 8 mm) of the path variation unit is so large that it is possible to scan from the front of the cornea up to the rear of the lens.

A single measurement thus processes the reflections from several regions together nearly simultaneously. In order, nevertheless, to be able to distinguish individual reflections by measurement, the measuring beams have different optical properties such as a different direction of polarization, a different wavelength, . . . However, it is also possible to work with non-distinguishable beams and to bring the two interference signals into congruence by varying the detour, In this case, the detour set is then equal to the desired distance, thickness etc. The use of non-distinguishable beams leads to a loss in sensitivity.

Depending on the number of measuring beams used, it is possible to determine one or more distances with one measurement. As described in WO 96/35100, the changes in path length in the reference arm can be undertaken with a rotating transparent cube upstream of a stationary reflector. Such a cube can rotate without difficulty at over 10 Hz. That is to say, in the case of most measurements the object to be measured can be regarded as being at rest without providing special arrangements for fixing it.

The detour is produced with a detour unit in which the geometrical-optical length of the detour can be varied with reference to one of the beam splitters by adjusting the distance of a deflecting mirror. The beam splitter and each deflecting mirror assigned to the latter are, in particular, aligned relative to one another in such a way that each deflected measuring beam with the non-deflected one has a single optical axis inside the object and, optionally, one focusing unit each for each measuring beam, in order to be able to focus the latter onto one region each. Such an arrangement can be used to measure thickness, length and/or distance, and/or to measure the thickness, length and/or distance profile.

It is preferred to make use in the device of a memory unit in which it is possible to store path lengths of the path length variation unit, in the case of which path lengths it is possible to store an interference of the first and third as well as of the second and third measuring beams. The thickness, length and/or distance value will then be determined in conjunction with first and second measuring beams preferably approximately focused on one axis, and/or a surface profile will optionally be determined from the stored data in conjunction with first and second beams situated laterally in a neighboring fashion.

Further design variations relating to the invention, and their advantages emerge from the following text. It may be remarked in general that the following optical units designated as beam splitters can undertake beam splitting, or else a combination of two beams.

BRIEF DESCRIPTION OF THE DRAWINGS

Examples of the device according to the invention with the aid of which the method according to the invention can be carried out are explained below with the aid of drawings, in which.

WAYS OF IMPLEMENTING THE INVENTION

Figure 1:
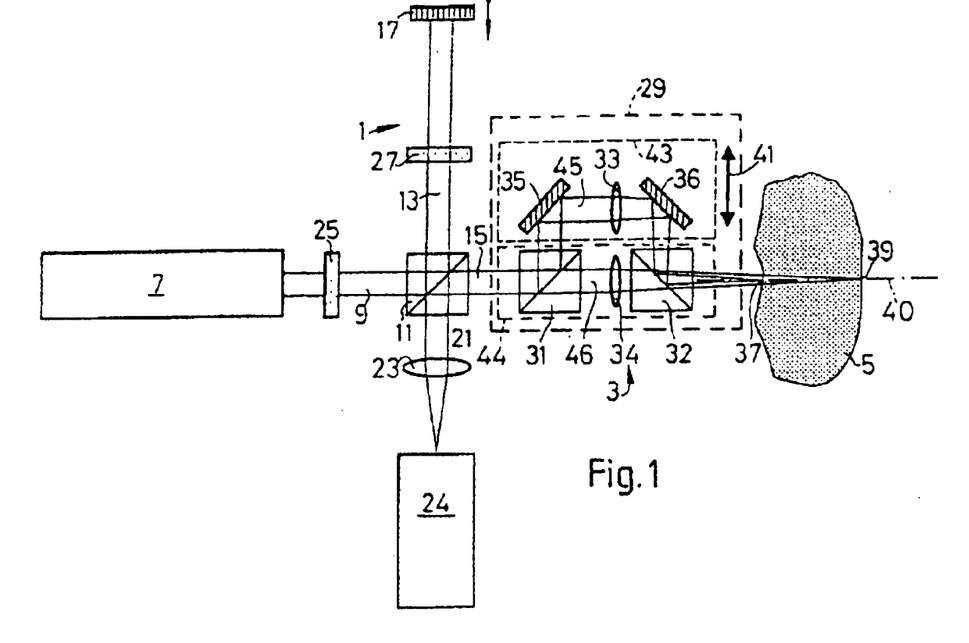
FIG. 1 shows an optical block diagram of a device according to the invention.

An exemplary embodiment of the device according to the invention with an optical arrangement of the Michelson interferometer type is illustrated in FIG. 1. The optical arrangement has a reference arm 1 and a measuring arm 3, in which the object 5 to be measured is arranged. A radiation source 7 emits a parallel source beam 9 with a linearly polarized short coherence radiation. The coherence length of the radiation is selected to be shorter than the distances in the object 5, which are described below and are to be measured. The source beam 9 emanating from the radiation source 7 is split with a physical beam splitter 11, which does not vary the polarization of radiation, into a reference and an object beam 15 for the measuring arm 3. By contrast with a geometrical beam splitter, the original beam cross section is maintained in a physical beam splitter. The light power is split, as a result of which its radiance is also changed. The reference beam 13 is reflected back into itself at a path length variation unit, which is illustrated only diagrammatically and designed as a mirror 17 which can be displaced by translation. Radiation reflected by the object 5 is then superimposed on it in an interfering fashion in the beam splitter 11. This interfering radiation 21 is detected by focusing with a focusing unit 23 of a photodetector 24. Another path variation unit 17 which can be used by way of example is described in WO96/35100 as transparent cube rotating in the hertz range and integrated schematically in FIG. 2 in the optical design shown there. Of course, instead of a rotating cube it is also possible to use other path length variation units. For example, it is also possible to use a translatory mirror which "rocks to and fro" shown here. This "rocking" mirror could be a loudspeaker diaphragm provided with a reflecting coating. Arranged in the source beam 9 between the radiation source 7 and beam splitter 11 is an element 25 for rotating the direction of polarization of the source beam 9. A further element 27 for rotating the direction of polarization is arranged between the beam splitter 11 and path length variation unit 17. The elements 25 and 27 are designed here as so-called λ/2 and λ/4 plates (quarter-wave plate), respectively.

A detour unit 29 is inserted upstream of the object 5 in the measuring arm 3. The detour unit 29 has two polarization-sensitive beam splitters 31 and 32, two focusing units, which are illustrated symbolically by the lenses 33 and 34, and two deflecting mirrors 35 and 36. Since the depth of the transparent object 5 is to be determined in the example set out here, the focal length of the focusing unit 33 is selected in such a way that its focal point lies on the front surface 37 of the object. The focal length of the focusing unit 34 is selected in such a way that its focal point lies on the rear 39 of the object. The optical subsystem 43 [▶ deflecting mirror 35—focusing unit 33—deflecting mirror 36 ◀] can be displaced parallel to the optical subsystem 44 [▶ beam splitter 31—lens 34—beam splitter 32 ◀], as indicated by the arrow 41. The optical path of the radiation running through the subsystem 43 can be varied by displacement in the direction of the arrow 41. Since the measuring radiation is reflected in or on the object 5, the optical subsystems 43 and 44 are traversed twice. The optical path difference (only outward or return pass) is now set in such a way that it corresponds approximately to the optical distance to be measured in the object 5, here the optical object depth.

The mode of operation of the λ/2 and λ/4 plates 25 and 27, respectively, is left out of the following description of the measuring method for the time being. The linearly polarized source beam 9 emitted by the radiation source 7 strikes the beam splitter 11 and is split by the latter into equal parts of the reference arm 1 and the measuring arm 3 as reference beam 13 and object beam 15. (It is not, however, absolutely necessary to split into equal parts.) The beam splitters 31 and 32 are designed as polarizing beam splitters. The beam splitter 31 is designed and orientated in such a way that the polarized source beam 9 split by the beam splitter 11 strikes the beam splitter 31 with half the intensity of radiation as object beam 15 with a direction of polarization within 45°. Here, the object beam 15 is split into two measuring beams 45 and 46, whose planes of polarization are now situated rotated by 90° relative to one another. The reference beam 13 polarized within 45° therefore contains these two directions of polarization. Whenever interference can be detected, the length of the optical path ▶ beam splitter 11—beam splitter 31—focusing unit 34—beam splitter 32—rear of the object 39 and back again ◀ is of the same length as that path which is traversed by the reference beam 13 reflected at the mirror 17, it being possible to vary the optical path length in the reference arm 1 in the hertz range with the path length variation unit 17. The focusing unit 34 can be omitted in certain applications. For example, for the purpose of measuring eye length the focusing of the measuring beam 46 can be taken over by the reflective power of the eye. An assignment of length is possible via the respective angle of rotation of the unit 17. (The displacement can be detected at the translation stand in the case of a linearly displaceable mirror.) A further interference can be detected when, in a way similar to the statements just made, the optical path [▶ beam splitter 11—beam splitter 31—deflecting mirror 35—focusing unit 33—deflecting mirror 36—beam splitter 32—front of the object 37 and back again ◀] is the same length as the reference beam 13 reflected at the mirror 17. If the path difference through the detour unit 29 corresponds to the distance on the front to the rear of the object 37 and 39, respectively, the instances of interference coincide in the case of one and the same position of the mirror 17 (path length variation unit). If this is not so, only slightly different positions result by comparison with the actual distance (thickness).

The optical path length differences of the two optical paths in the detour unit 29 are always set such that they would correspond to an approximate measurement result to be expected. That is to say, the measurement thus always determines only the deviation from the measurement result to be expected. Since these deviations are always significantly smaller than when the whole path (distance, thickness, . . . ) has to be measured, it is possible to work with a significantly smaller and thus quicker path length variation in the reference arm. That is to say, in terms of time, the two instances of interference occur very quickly in sequence; they can even occur simultaneously. Since in the case of distances, thickness measurements, . . . two temporally staggered measurements were always to be undertaken in the prior art, in the case of the invention the measurement result is now available quickly in such a way that spatial displacements of the object to be measured influence the measuring accuracy only insubstantially. The beam splitters 31 and 32, the deflecting mirrors 35 and 36 and the two focusing units 33 and 34 are arranged in the detour unit 29 in such a way that the two focal points lie on the front 37 and the back 39 of the object on an optical axis 40.

The advantage just outlined is of great benefit in an eye length measurement for the eyes of children, who are generally difficult to keep still.

If it is desired to assign the instances of interference which occur to the relevant reflecting surfaces, it is possible to make use of, instead of one photodetector 24, two, one for each direction of polarization. The radiation of one direction of polarization is then directed by means of a polarizing beam splitter onto one photodetector, and the radiation of the other direction of polarization is directed onto the other photodetector.

The radiation can now be reflected at different levels at the front and at the rear of the object 37 and 39, respectively; again, there can be differences between reflections on regions inside an object whose distance apart it is desired to determine or, in this case of layers, whose thickness it is desired to determine. In order now to be able to adapt the reflective intensity within certain bounds, the λ/2 and λ/4 plates 25 and 27, respectively, are present in the source beam 9 and in the reference beam 13. It is now possible to adjust the respective plate in such a way that more intensity is injected in the beam whose radiation is weakly reflected.

The change in path length in the reference arm 1 imparts to the radiation frequency of the reference beam 13 a Doppler frequency $f_{Doppler}$ in accordance with the relationship $$f_{Doppler} = \frac{2 \cdot f_0 \cdot v_{scan}}{c},$$

$f_0$ being the radiation frequency of the radiation source 7, $v_{scan}$ the rate of change in the path length, and c the speed of light. (The Doppler frequency $f_{Doppler}$ is approximately constant with the path length variation unit described in WO96/35100.) The interference signal detected with the photodetector 24 also has this Doppler frequency. The electric signal received by the detector 24 can therefore be separated with an electronic bandpass filter from the remaining detected radiation. It is thereby possible to improve the signal-to-noise ratio considerably.

Figure 2:
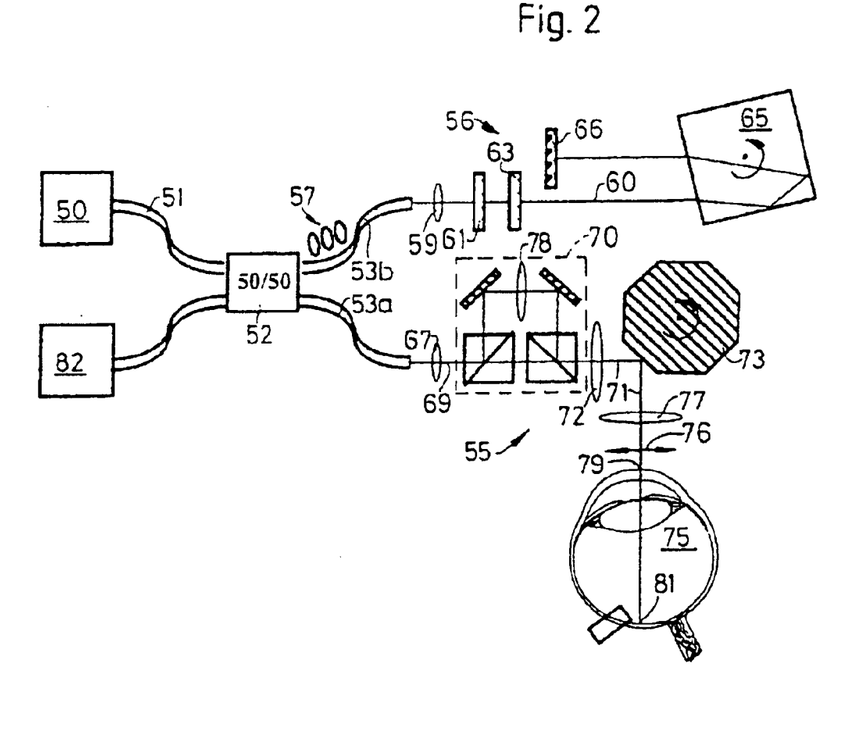
FIG. 2 shows a variant of the optical arrangement in FIG. 1.

As illustrated in FIG. 1, not all beam paths need now run as free "space beams". As illustrated in FIG. 2, it is also possible to use fibers as radiation conductors. In a way similar to the radiation source 7, in FIG. 2, use is made of a laser diode 50, a superluminescence diode, LED or another broadband light source whose radiation is guided via a radiation conductor 51 to a fiber coupler 52. The radiation of the laser diode 50 is split in the fiber coupler 52 into the two radiation conductors 53a and 53b, the radiation conductor 53a being a component of the measuring arm 55, and the radiation conductor 53b a component of the reference arm 56.

In a fashion similar to the λ/4 plate 27, a fiber polarization controller 57 is integrated in the radiation conductor 53b of the reference arm 56. Arranged at the end of the radiation conductor 53b averted from the fiber coupler 52 is a collimator 59 which converts the radiation emerging from the conductor end into a parallel free-space beam 60. The intensity of this free-space beam 60, particularly in relation to the radiation reflected in the measuring arm 55, can subsequently be varied at the collimator 59 with a gray filter 61 (damping) and a further λ/4 plate 63. By contrast with a reference mirror 17 which can be displaced by translation, use is made in FIG. 2 as path variation unit of a rotating transparent cube 65 with a mirror 66 which reflects the radiation falling onto it back into itself (WO 96/35100).

Arranged in the measuring arm 55 at the end of the radiation conductor 53a applied to the fiber coupler 52 is a collimator 67 which transforms the radiation emerging from the conductor end into a parallel free-space beam 69. As already set forth above, the free-space beam 69 is split with a detour unit 70, of similar design to the detour unit 29, into two measuring beams having different transit times, and once again superimposed with a common optical axis as common beam configuration 71. The beam configuration 71 having the two measuring beams traverses a lens system 72 for minimizing the beam diameter onto the polygonal surfaces of a rotating polygonal mirror 73. As a consequence of the rotation of the polygonal mirror 73, the beam configuration 71 is deflected over the eye 75 in the direction of the arrow 76 shown there. It is thereby possible to record an eye length profile. Using the stored values of a surface, the surface profile thereof can be determined with reference to a reference plane, as described below (see FIG. 6). Using the lens system 67 and a lens system 78 in the detour, adapting the focal points of the two measuring beams is undertaken in such a way that as a consequence of the lens systems 67 and 78 and of the lens systems 72 and 77 the beam having the detour being focused onto the cornea 79 of the eye 75, and the measuring beam not having the detour is focused onto the eyeground. It is thereby possible to undertake an eye length measurement.

The radiation retroreflected in the reference arm 56 and superimposed with a Doppler frequency is then superimposed in an interfering fashion in the fiber coupler 52 onto the radiation, retroreflected in the measuring arm 55, from the eye 75 and detected, in a fashion similar to the above exposition, by the detector 82 connected via a radiation conductor 80 to the fiber coupler 52.

Instead of only a single polygonal mirror, it is, of course, also possible to make use of two, in order to achieve two-dimensional coverage (scanning). Instead of a regular polygonal mirror, it is also possible to use a polygonal mirror whose reflecting surfaces exhibit a successive varying angle of inclination to the axis of rotation, in order to achieve line-type scanning. The rates of rotation between the "cube" of the path variation unit and the polygonal mirror need not be coordinated; only the respective positions need be known for the computerized evaluation.

Instead of a polygonal mirror, it is also possible to use so-called galvanometer mirror, electrooptical and acoustooptical reflectors. Again, it is possible to use an electromagnetically moved mirror which is mounted on a spherical surface in such a way that two-dimensional deflection is possible. The advantage of this arrangement by comparison with a polygonal mirror is a fulcrum near the mirror surface.

Figures 3, 5:
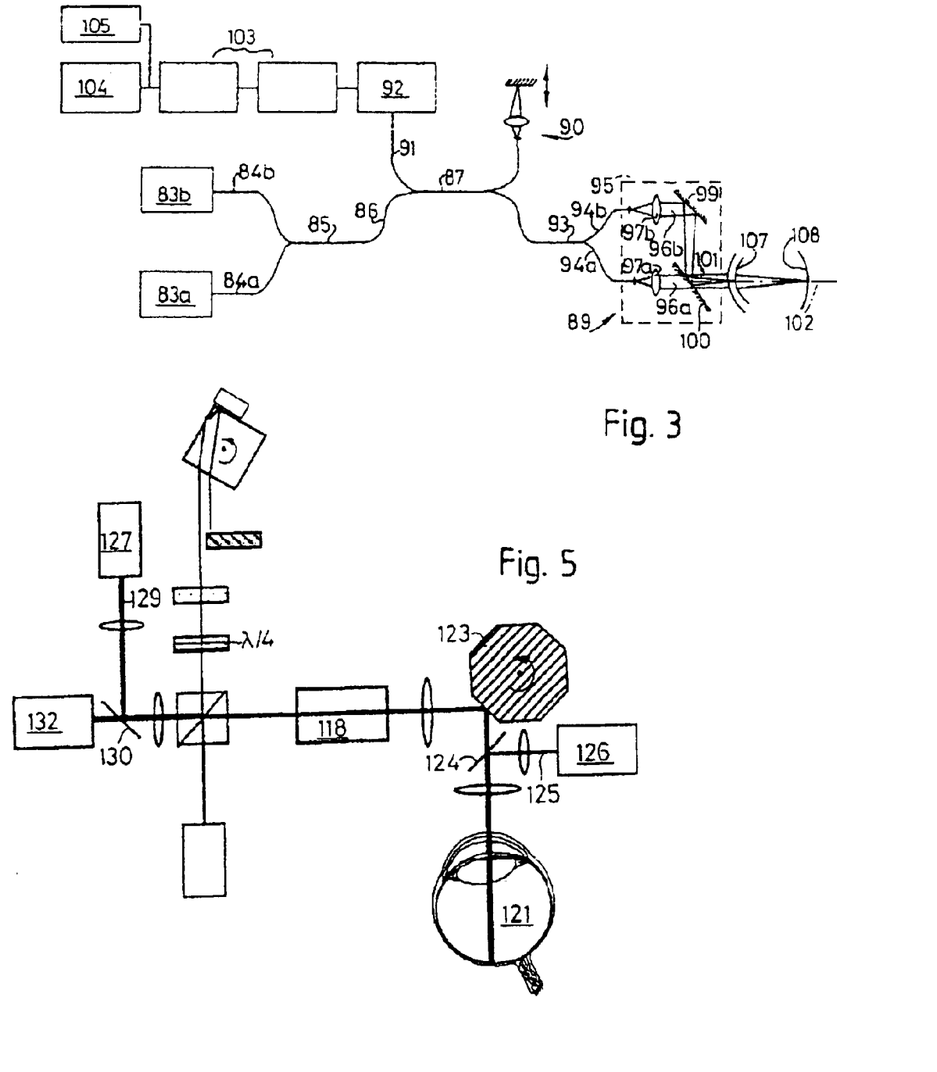
FIG. 3 shows a further variant of the devices which are illustrated in FIGS. 1 and 2, but which work here with two different center wavelengths.
FIG. 5 shows a variant of the devices illustrated in FIGS. 1 to 4.

FIG. 3 shows, in addition to the optical arrangements illustrated in FIGS. 1 and 2, a further design variant of the invention in the case of which use is made of two radiation sources 83a and 83b with different center wavelengths. The spectra of the light sources used should overlap one another as little as possible. In a fashion similar to the optical design in FIG. 2, radiation conductors are also used here. In a first fiber coupler 85, the radiation conductors 84a and 84b proceeding from the two radiation sources 83a and 83b are coupled into a radiation conductor 86, which is connected to a further fiber coupler 87. Departing from the fiber coupler 87 are a measuring arm 89 and a reference arm 90, as well as a radiation conductor 91 going to a detector 92. By contrast with the design variants already described above, here the measuring arm has a further fiber coupler 93, with the aid of which the radiations, coming from the two radiation sources 83a and 83b, with different center wavelengths are split again into two radiation conductors 94a and 94b in accordance with the center wavelengths. The ends of the two radiation conductors 94a and 94b terminate in a detour unit 95. The detour unit 95 has one lens system 97a and 97b each for the free-space beams 96a and 96b emerging from the ends of the radiation conductors 94a and 94b. The free-space beam 96b is then combined via a deflecting mirror 99 with a wavelength-selective beam splitter (combiner) 100 to form a beam configuration 101 having a single optical axis 102. The lens systems 97a and 97b are now selected precisely in such a way that the relevant free-space beam 96a or 96b is focused onto the relevant splitting surface, here 107 and 108, for example, for the purpose of determining thickness and/or distance. In the design variant described here, it is easy to adjust the detour by, for example in accordance with the illustration in FIG. 3, merely displacing upwards the deflecting mirror 99 together with the lens system 97b and the end of the beam splitter 94b with reference to the beam splitter 100. This can be carried out easily, since the radiation conductors 94a and 94b are flexible.

The electric "interference signals" received by the photodetector 92 are then processed further with the aid of an electronic evaluation system 103 and, when appropriate, displayed on a display screen 104, and can be passed on via a data transmission network 105 for further processing and storage.

There is no need either for the abovedescribed different polarization or for the two different wavelengths in the deflected and in the direct beam of the measuring arm in order to take measurements at two regions in an object which are situated separately in the axial direction. It is then likewise possible to dispense with the λ/4 and λ/2 plates. The polarization-sensitive or wavelength-sensitive beam splitters or fiber couplers can then be replaced by normal physical beam splitters. An advantage of working with different beam properties [different frequency, different direction of polarization] presides in an increase in sensitivity by the factor 8. Specifically, if radiation that cannot be distinguished is used, half the radiation is "lost" on the outward path at the beam splitter 32 or 100, and half is lost twice, in addition, on the return path. Specifically, firstly at the beam splitter 32 or 100 both for the radiation reflected by the front of the object and for the radiation reflected by the rear of the object. This radiation is "lost" for interferometric detection owing to the "wrong" detour because of the "wrong" wavelength. Furthermore, once again half the radiation is lost at the beam splitter 31 or the fiber coupler 93, both for the radiation reflected by the front of the object and for the radiation reflected by the rear of the object. If an adequate radiation intensity is present, and if the object withstands this high intensity, this is a preferred design variant, since the optical components to be used are more cost effective here.

Figure 4:
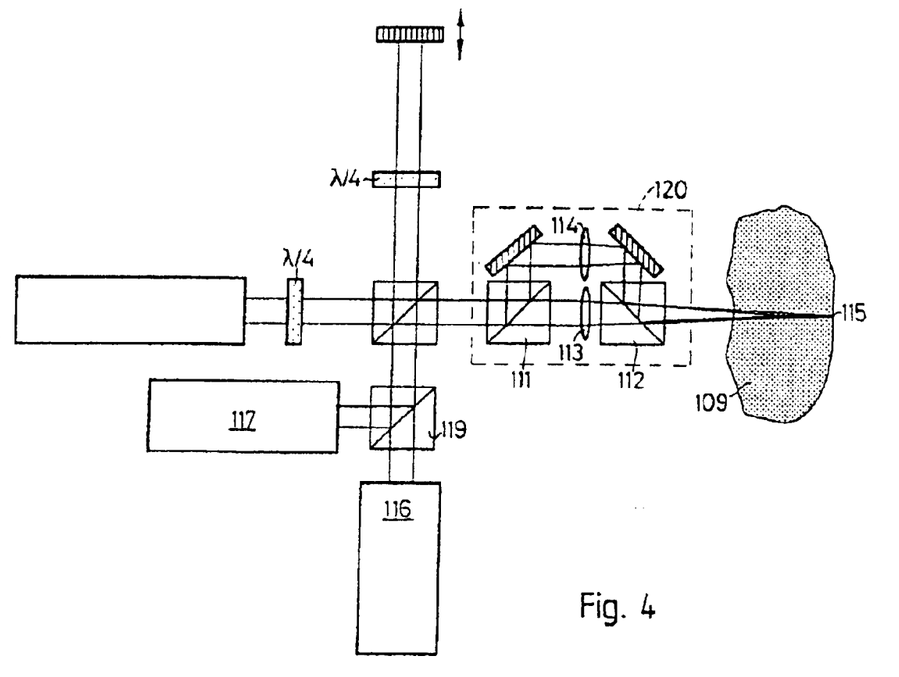
FIG. 4 shows an optical block diagram similar to FIG. 1, but determining the phase delay in a birefringent material.

If the phase delay is to be measured in a birefringent material of an object 109, use is made of a device with an optical design in accordance with FIG. 4. The design illustrated in FIG. 4 corresponds to that of FIG. 1, except for the differences listed below.

In FIG. 4, the beam splitters 31 and 32 of the design of FIG. 1 are the analogous beam splitters 111 and 112.

Furthermore, the lens systems 113 and 114 corresponding to the lens systems 33 and 34 are designed in such a way that the focal points they generate coincide in a region, here on the rear of the sample, for example; the aim, after all, is to determine a phase delay of the two beams with planes of polarization perpendicular to one another. Instead of a single photodetector in FIG. 1, there are now present in FIG. 4 a photodetector 116 and 117 for each direction of polarization, the beam falling on them and reflected by the rear of the sample 115 and on which the reference beam is superimposed in an interfering fashion being split by a polarizing beam splitter 119.

The p-polarized radiation reflected by the rear of the sample 115 is radiated with negligible losses on the short path through the detour unit 120 via the beam splitter 119 onto the photodetector 116. The s-polarized radiation likewise reflected by the rear of the sample 115—the plane of polarization of the s-radiation is perpendicular to that of the p-radiation—is likewise radiated with negligible losses on the long path through the detour unit 120 via the beam splitter 119 onto the photodetector 117. Since it is exclusively radiation reflected by the rear of the sample 115 which is detected, the detour unit 120 is to be set in such a way that the optical path differences between the s- and p-radiation are as small as possible. It is then possible to reach a conclusion on the phase delay of the birefringent material from the intensities, measured by the photodetectors 116 and 117, of the relevant reflected intensities.

If, in addition to one of the abovedescribed measurements it is also intended to carry out an observation, it is then possible, for example, to use a device with an optical design as shown in FIG. 5. The optical arrangement of FIG. 5 corresponds essentially to the arrangements shown in FIGS. 1 to 4. A detour unit 118 corresponding to the detour units 29; 70 and 120 is merely indicated. The design variant in accordance with FIG. 5, however, exhibits the following differences. Present downstream of a polygonal mirror 123 already described in FIG. 2 for the purpose of illuminating the object, here an eye 121, is a beam splitter 124 via which the illuminating beam 125 of a radiation source 126 is coupled in. The region to be measured can be observed with a camera 127 and reproduced on a monitor (not illustrated). The observing beam 129 is directed with a beam splitter 130 onto the camera 127. If the observing beam appears on the monitor 128 within a specific spatial tolerance range, the eye is aligned and the measurement can be initiated.

If the aim is to determine very small thicknesses or distances, it can happen that the detour shown in FIGS. 1 to 5 in the detour unit sketched there is too long as a consequence of the geometrical dimensions of optical components to be used. It is possible in this case, by analogy with the large optical path respectively shown there, also to lengthen the short optical path in which here, as well, two displaceable deflecting mirrors are inserted into the beam path. Arbitrarily short and long detours can then be interchanged with such a detour arrangement.

Figure 11:
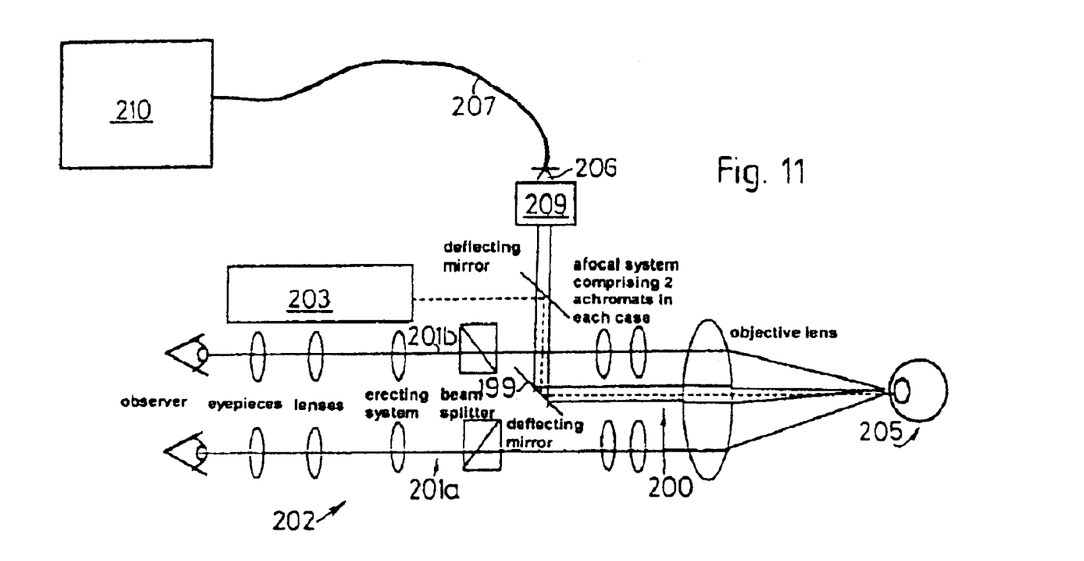
FIG. 11 shows a schematic illustration of a stereomicroscope of a slit-lamp unit with a measuring beam path in the middle channel of the microscope.

In addition to its design variants, the above-described device according to the invention can be used together with already existing units. This device can, for example, be installed in a slit-lamp unit for ophthalmology, or be combined therewith. The measuring beam can then be coupled as free-space beam either via beam splitters into the illuminating beam path, in the case of a microscope likewise via beam splitters into an observation beam path or at the microscope objective, or with a deflecting mirror 199, into a middle channel 200 of a stereomicroscope 202 of a slit-lamp unit, as shown in FIG. 11. The middle channel 200 lies between the two beam paths 201a and 201b of the stereomicroscope 202. In addition, the fixation light source 203 is also shown in FIG. 11. By viewing the fixation source 203, the patient aligns his eye 205 with a prescribed location and mostly also holds it fixed on the latter without movement. The measuring beam 206 emerges (in a fashion similar to the device arrangement as shown in FIG. 2) from a fiber 207 and traverses a detour unit 209, which is designed in a way similar to the detour unit 29, 70, 89 or 120, is not explicitly illustrated and has an optional transverse scanner. The remaining elements of the device according to the invention are installed in a compact base unit 210. When selecting the lenses used in the detour unit 209, it is merely necessary also to take account of the lens action of the objective lens of the slit-lamp microscope 202.

By adjusting the slit-lamp unit into three spatial coordinates, preferably a so-called steering level, the measuring beam is also then adjusted accordingly. Instead of adjusting the entire slit-lamp unit together with the measuring beam, it is also possible to adjust the two independently of one another. As already indicated above, when adjusting only the measuring beam it is preferred to use a "fiberoptic" design similar to the illustration in FIG. 3.

In the case of a combination with a video-keratograph equipped with Placido's disk, the measuring beam is coupled in in the direction of the illumination axis of the video-keratograph with the aid of a small beam splitter.

Figure 12:
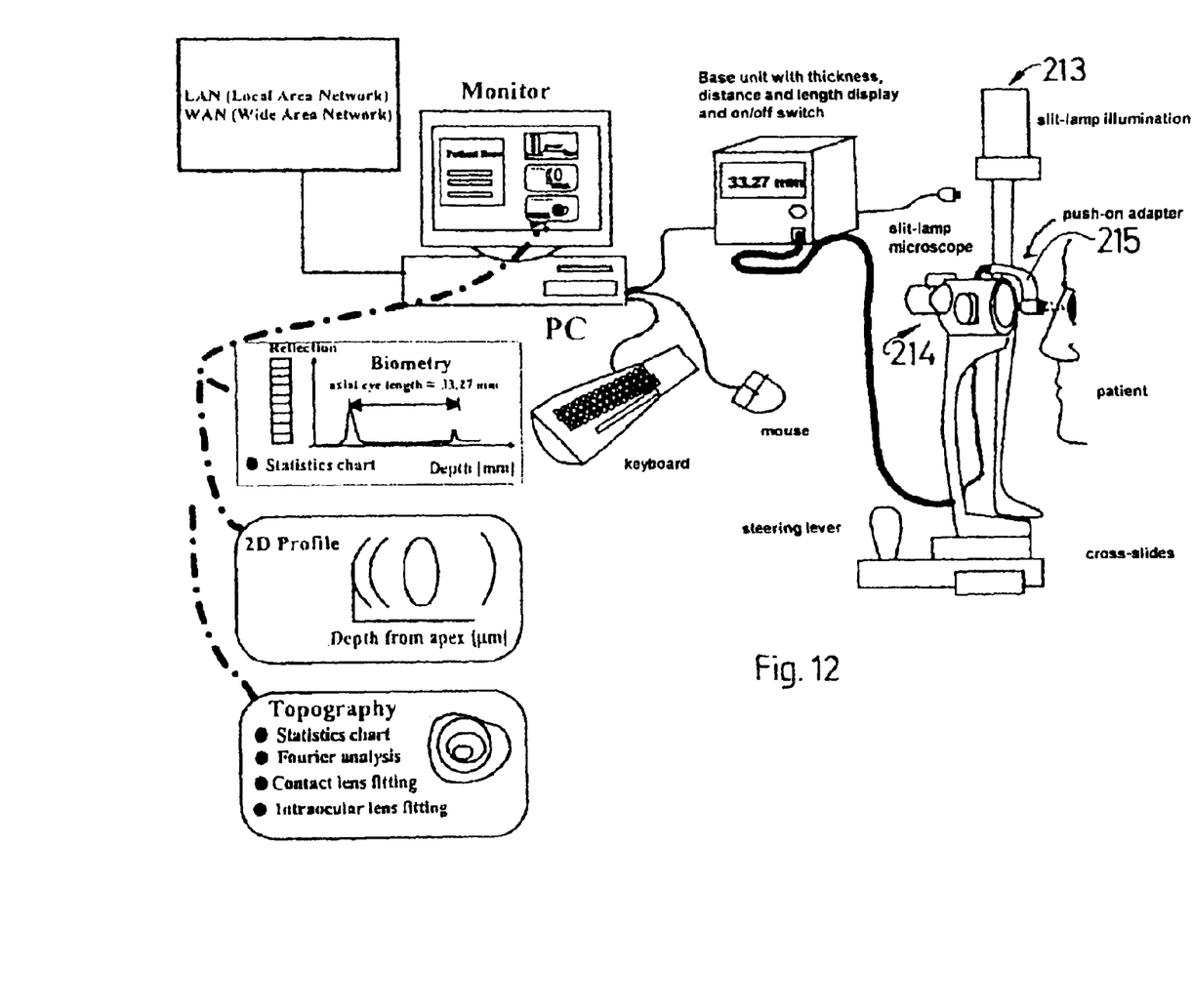
FIG. 12 shows a slit-lamp unit with an adapter which can be pushed onto the microscope.

Instead, as described above, of integrating the measuring beam path in a stereomicroscope, in the case of a slit-lamp unit 213, it can also be supplied via an adapter 215 which can be pushed on to the microscope 214, as is sketched in FIG. 12. The adapter 215 includes the functions of the detour unit 29, 70, 95 or 120.

On the basis of the above exposition, the device in accordance with FIGS. 1 to 5 can be combined with various units. However, since the measuring operation is performed extremely quickly, it can also be designed as a handheld unit which is then simply held in front of an object to be measured. In the case of a design as a handheld unit or as a modified slit-lamp unit (FIG. 12), it is preferred to use the design variant, shown in FIG. 3, with fiber conductors, since this provides a wide freedom of movement. In this case, the movable fibers are preferably designed as polarization-maintaining fibers. Also possible, for example, is a combination with a so-called contact lens which, held in the hand, is placed on the surface of the cornea of the human eye.

In order to design this device to be capable of as universal a use as possible, it would now be necessary for the path length variation element to be able to traverse a large variation path, since the length of the measuring arm (distance from the detour unit to the object to be measured) can vary strongly. Specifically, instances of interference arise only when the reference path and corresponding measuring path are of the same length. The path length variation element must be capable of equalizing these differences. A large variation path on the one hand entails an expensive design of the path length variation unit and, in addition, lengthens the measuring time.

This disadvantage can be circumvented by attempting to keep the measuring path within small tolerance paths. Two beams from the radiation source can now be arranged in such a way that they do not strike the object to be measured in the measuring region until said object is located within a prescribed distance. For this purpose the two adjusting beams (pilot laser) will be radiated in a fashion inclined to the optical axis. For adjustment purposes two points are then viewed on a scattering or reflecting surface of the object to be measured, which merge to form one point only given the correct focusing.

In the case of the use of a viewing microscope, the detour can be set optimally in the detour unit by setting the beam diameter of each measuring beam minimally to the relevant region. This process can also be automated; for example, with a CCD camera, an evaluation and control unit and an actuator. The control unit used to control the actuator regulates the distance between the detour unit and the object to be measured (object).

Instead of only measuring one distance or one thickness in each case, it is also possible to measure a plurality by providing a plurality of detours instead of only one. Further detours can be obtained by in each case replacing a deflecting mirror by a beam splitter with appropriate properties and then again making use of a pair of deflecting mirrors or only a single deflecting mirror in the case of the fiber arrangement in accordance with FIG. 3.

Figure 6:
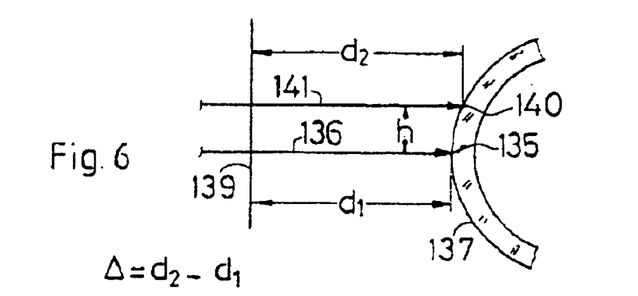
FIG. 6 shows an auxiliary illustration for explaining determination of a surface profile.

Measurements in the case of which a thickness is determined are carried out in FIGS. 1 to 5 described above. For this purpose, the first measuring beam is focused on to a first point and the second measuring beam, as a rule the one which has not traversed the detour, is focused on to a second point situated downstream of the first point. The first and second points are situated here on one optical axis. The device according to the invention can now also be designed and transformed in such a way that the focal points of the two measuring beams are situated next to one another. If the measuring beams are laid laterally next to one another, it is possible to determine a surface profile in the case of a surface which has a minimum reflection factor of $10^{-4}$%. As indicated in FIG. 6, for this purpose the distance $d_1$ of a first reflecting location 135 of the first measuring beam 136 on the surface 137 from a reference point or a reference plane 139 and the distance $d_2$ of the second reflecting location 140 of the second measuring beam 141 from the reference plane 139 is determined. Both measured values are stored in a memory unit 143. The distance difference $d_1$ and $d_2$ of the two measuring beams 136 and 141 of the reference plane 139 in relation to their mutual spacing h then yields two surface coordinates. These two coordinates can then be used to infer the surface profile with the aid of approximation methods if the type of surface is known. The type of surface is known in the case of the human eye. The surface can be determined more accurately if a plurality of measuring beams are used, or a plurality of measurements are undertaken with laterally offset measuring beams.

When fitting intraocular lenses in cataract treatment, an important role is played in ophthalmology not only by the eye length and the depth of the anterior chamber but also by curvature profile of the cornea, above all at the center of the cornea. All these values can be determined with the device according to the invention.

In the least demanding case, two specific radii of curvature of the central cornea, to be precise one radius of curvature in the horizontal direction and one in the vertical suffice for determining the profile. If these two radii differ, a (central) astigmatism is spoken of. The radii of curvature can be determined with the aid of known geometrical algorithms when, starting from a reference plane (here 139), the distance at a prescribed angle (here the normal distance $d_1$ and $d_2$) and the distance (here h) of the curve points (here 135 and 140) from one another are known per arc to be determined, as already set forth above. The distances $d_1$ and $d_2$ can be determined from the instantaneous location of the deflecting mirror in the relevant path length variation unit in the event of the occurrence of an interference phenomenon.

Use is made of a prescribed mirror position as reference value. If a path length variation unit with a rotating cube (as for example described in WO 96/35100) is used, it will be preferred to use as reference its zero degree position, in the case of which the incident beam strikes the first cube surface perpendicularly. Instead of the minimum of three measuring beams, in order to determine the two central radii of curvature it is also possible to use a plurality of measuring beams so as to undertake a more exact measurement of the radii of curvature. Again, measurement of thickness and radii can be undertaken simultaneously, as is set forth below.

Figure 7:
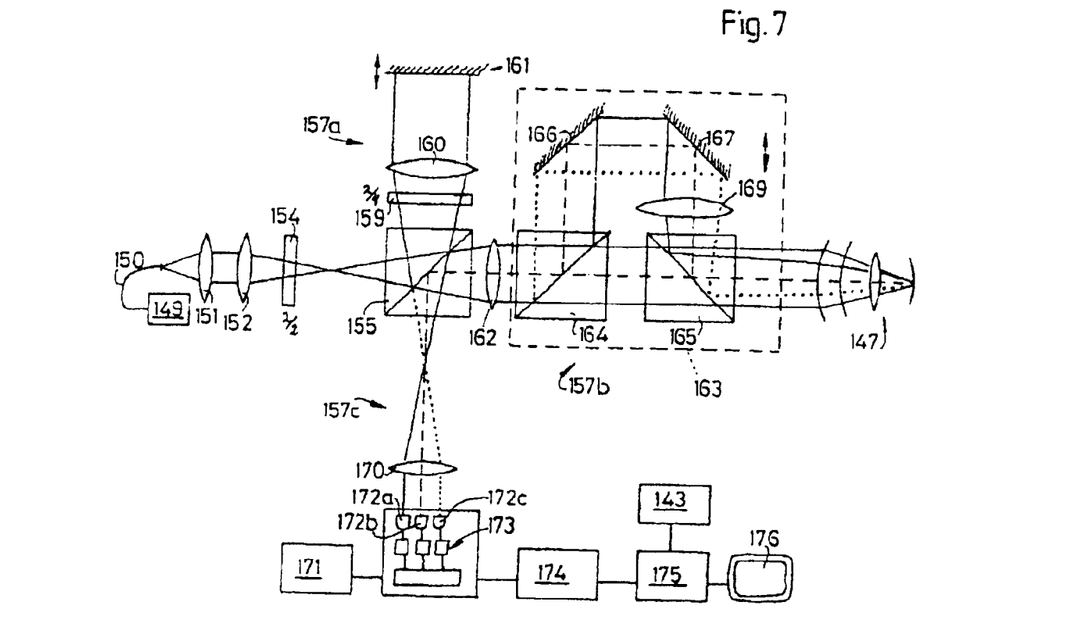
FIG. 7 shows an optical block diagram of a design variant for determining a surface profile together with various thicknesses.

The device described in FIG. 7 with the aid of an optical block diagram serves the purpose of determining a surface profile as well as various thicknesses in the case of a transparent or diffusive object, here a human eye 147. The optical design illustrated diagram-matically in FIG. 7 resembles that of FIG. 1 in large part. A radiation source 149 is also present here which may be a superluminescent diode, for example. The radiation from the radiation source 149 is here, however, guided by a radiation conductor 150 which permits the radiation source 149 and the measuring and evaluation unit to be independent of location. The radiation emerging from the radiation conductors 150 is collimated with a lens 151 and focused with a second, subsequent lens 152. A $\lambda/2$ plate 154 is arranged between the focal point 153 and the lens 152 for the purpose of "rotating" the direction of polarization of the radiation. There follows subsequently a beam splitter 155 with which the radiation is split into the measuring arm 157a and the reference arm 157b. Following the beam splitter 155, the reference arm 157a has a $\lambda/4$ plate 159, formed by a lens 160 with which the radiation coming from the beam splitter 155 is collimated. Merely a linearly adjustable mirror is indicated diagrammatically as path length variation unit 161; however, it is also possible to use units of other designs such as the rotating cube, for example.

Following the beam splitter 155 in the measuring arm 157b is a collimating lens 162, and then a detour unit 163, which is designed in a way similar to the detour unit 29 and has two polarizing, wavelength-sensitive beam splitters 164 and 165, two deflecting mirrors 166 and 167, and a focusing lens 169.

The radiation retroreflected by the eye is superimposed with the reference radiation coming from the reference arm 157a and guided in the detector arm 157c by a lens 170 on to a detecting array 171, there having been undertaken for the sake of simplicity only a linear and not a two-dimensional illustration of only three detectors 172a, 172b and 173c arranged next to one another. Connected downstream of each detector 172a, 172b and 173c is an electronic circuit 173, for example with an amplifier, Doppler frequency filter, rectifier and low-pass filter. The detected measuring signals are then processed via an analog-to-digital converter 174 and a computer 175 with the memory unit 143 and displayed on a display screen 176.

Figure 8:
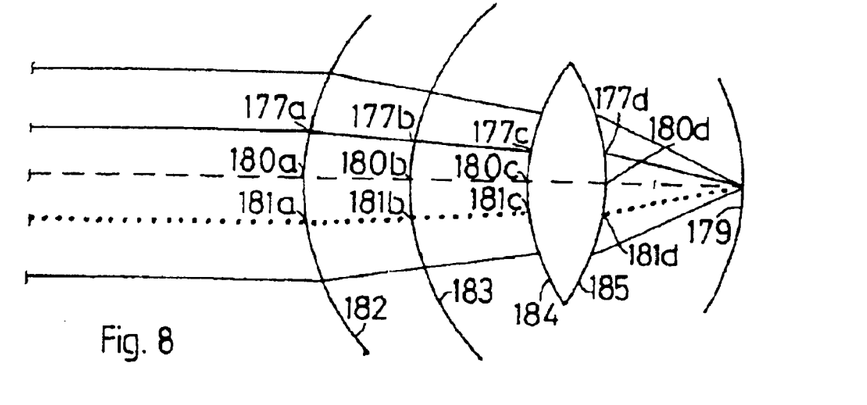
FIG. 8 shows an enlarged illustration of the beam path, shown in FIG. 7, directly in front of and in the eye 147.

The device illustrated diagrammatically in FIG. 7 can be used to measure the eye length, the cornea thickness, the depth of the anterior chamber, the lens thickness, the depth of the vitreous humor and the thickness of the retinal layer simultaneously at various points. Since measurements can be made at various points, it is also possible to determine surface profiles by calculation. In order to illustrate this, three laterally offset beam paths are illustrated with lines which are continuous, dashed and dotted, and which are guided to the detectors 172a, 172b and 172c. As is illustrated in an enlarged fashion in FIG. 8 for the purpose of greater clarity, the dashed beam comes from the locations 177a, 177b, 177c, 177d and the retina 179. Depending on the position of the mirrors 166 and 167 and of the mirror in the path variation unit, the detector 172a then records an interference signal. A similar statement holds for the locations 180a to 180d and 181a to 181d. A detector array comprising m×n photodetectors can be used to measure and evaluate simultaneously locations on or in the eye 147, for example on the front surface of the cornea 182, the rear surface of the cornea 183, the front and rear surface of the eyelid 184 and 185 respectively. After a certain time period which is a function of the rate of movement of the mirror in the path variation unit 161, beams guided to the locations marked with (b), then with (c), with (d) are detected and evaluated.

The lenses 160 and 162 can be designed as a one-dimensional or two-dimensional lens array, depending on use.

Figure 9:
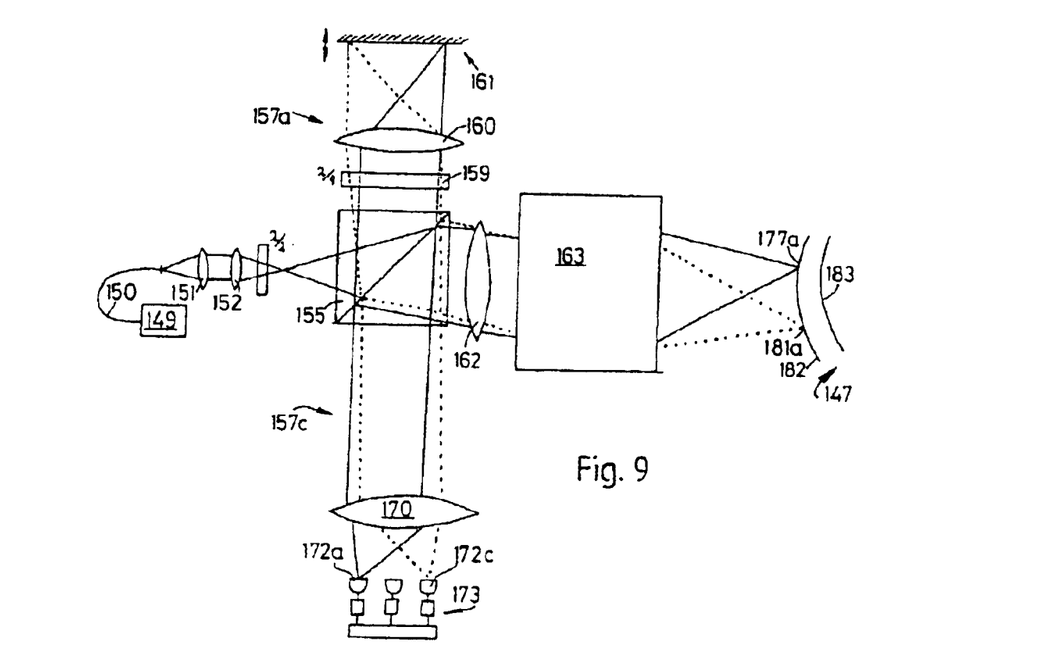
FIG. 9 shows a schematic illustration of the beam path, illustrated in FIG. 7, only for the edge beams of the beams falling onto the detectors 172a and 172c.

In addition, for the purpose of a better understanding of the measuring operation the "beam limits" to and from the location 177a are illustrated with continuous lines, and those to and from the location 181a are illustrated with dotted lines in the reference, measuring and detector arms 157a, 157b and 157c in FIG. 9. The continuous and dotted lines show the two edge beams in the reference, measuring and detector arms 157a, 157b and 157c, which permit the space coordinates of the location 177a and 181a to be measured, that is to say they interfere with these beams.

Figure 10:
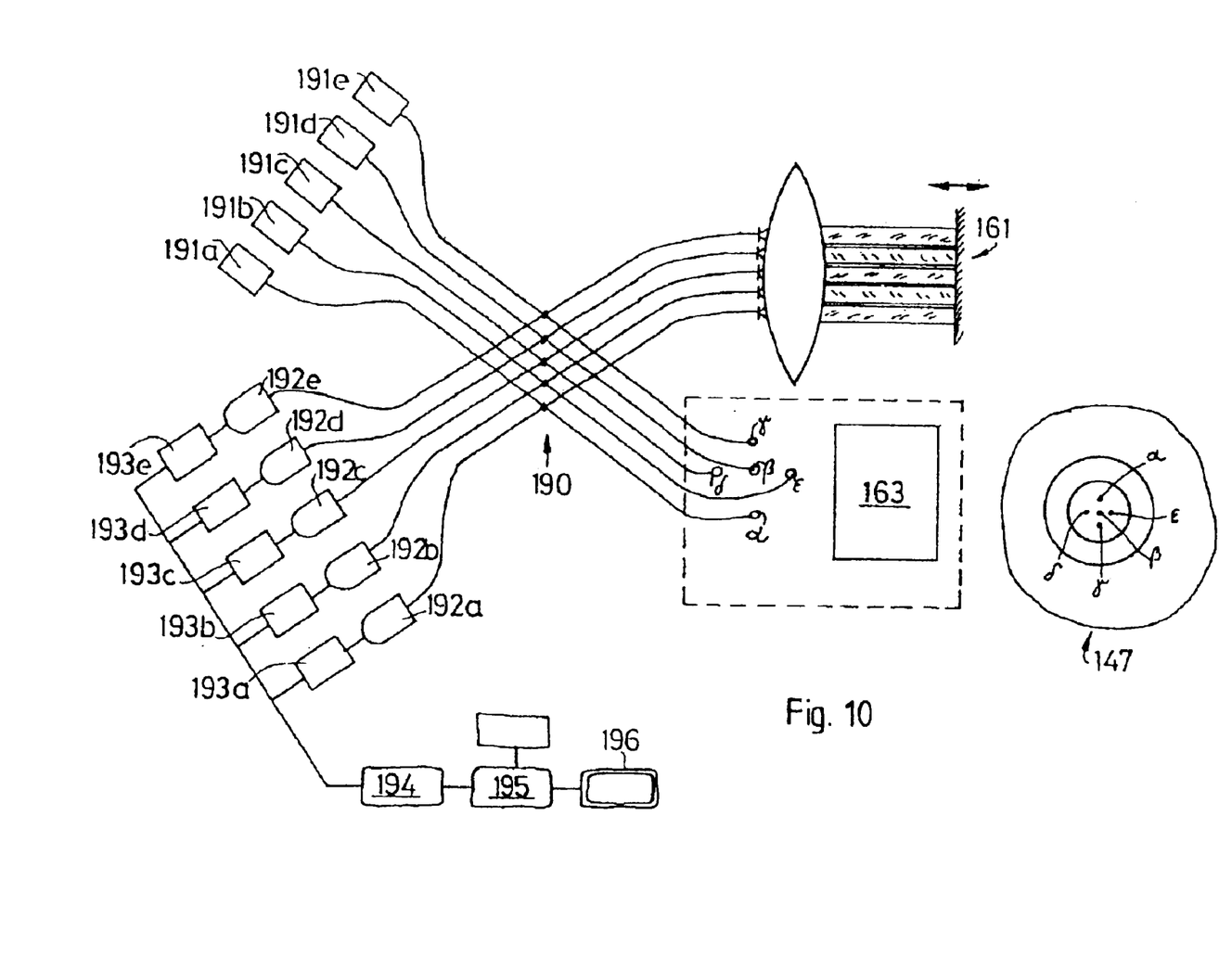
FIG. 10 shows an optical block diagram of a variant of the devices according to the invention, in the case of which the radiation runs for the most part in radiation conductors, the surface of the eye being drawn rotated by 90° in order to illustrate the locations of incidence of the beams.

A device to be designated as a fiberoptic-parallel, short-coherence reflectormeter is sketched in FIG. 10. This design variant of the invention permits, for example, simultaneous measurement of four central radii of curvature of the front surface of the cornea in the horizontal (left and right) and vertical (top and bottom) directions. In addition, it is also possible to measure four central radii of curvature of the rear of the cornea simultaneously. This device has five 2×2 single-mode fiber couplers 190, five radiation sources 191a to 191c, five detectors 192a to 192e with an associated circuit 193a to 193e, an analog-to-digital converter 194, computer 195 and display 196. The remaining elements and units (in particular 161 and 163) correspond to those of FIG. 7.

The calibration of the abovedescribed devices can be performed by coupling into the reference arm (for example 1 or 157a) the radiation of a high-coherence radiation source (for example, a distributed feedback laser) with a beam splitter (not illustrated). The radiation coupled in then interferes with a fraction of the radiation which is reflected at an arbitrary location between this beam splitter and the path length variator at a stationary reflector. The coherence of the high-coherence radiation source is greater than the path variation length of the variator. An interference fringe pattern then runs over the detectors (or on a detector specially set up for the purpose). The distance between in each case two interference fringes then corresponds in each case to half a wavelength. Path calibration of the path length variator is possible by (automatically) enumerating these fringes. Since the high-coherence radiation cannot reach the patient's eye, its radiant power can be relatively high, and so this detection is not critical. The wavelength of the high-coherence radiation can (although it need not) have the same wavelength as the short-coherence radiation used for the eye measurement.

The thicknesses of the cornea which are determined with the abovedescribed devices according to the invention can preferably be incorporated into a consultation with patients for whom the aim is to undertake refractive surgery with LASIK (laser-assisted in situ keratomileusis), in which, calculation of a difference relating to the critical cornea thickness with regard to the current cornea thickness is performed individually. The following novel steps are preferably undertaken for this purpose:
1. A preoperative central cornea thickness $d_z$ is determined with one of the devices as are shown in FIGS. 1 to 5, 7 or 10.
2. The mean flap thickness $d_f$ customary for LASIK of typically 160 μm is subtracted (adjustably) from the determined cornea thickness $d_z$.
3. A (maximum possible) pupil diameter is determined during which the eye is exposed to typical nocturnal conditions of light intensity. The "nocturnal pupil diameter" can be measured by darkening the examination space with a TV camera connected to the devices according to the invention or their design variants. Such a camera can be docked, for example in the detector arm via beam splitters with an appropriate lens system. The measurement of the pupil diameter is optional. Standard values can also be used for the consultation.
4. An optimum ablation diameter S is then stipulated for the cornea, the diameter being required to be larger than the nocturnal pupil diameter, in order to avoid halo phenomena after the ablation.
5. The correction in diopters to be achieved with LASIK is known from the previous measurements (for example, from a knowledge of the refractive power of an already used pair of spectacles or contact lenses already owned by the patient).
6. The central ablation depth to [in micrometers] required for the desired correction is calculated for the desired correction using the formula $t_0=-(S^2D)/3$, S being the optimum ablation diameter in millimeters and D the desired change in diopters as a consequence of the ablation.
7. The central stromal residual thickness $d_s=d_z-d_f-t_0$ which would be obtained after the LASIK operation is now calculated.
8. It is clarified whether the residual thickness d, is above a critical central stromal residual thickness $d_k$. A possible definition for the critical central stromal residual thickness $d_k$, is, for example, $d_k=a \cdot d_z-b$, and a=0.58 and b=30 μm being adopted as standard values.
9. If, now, $d_s$ is greater than $d_k$, it is possible to recommend a LASIK operation.

The processing steps set forth above can, of course, be automated via a computer.

The procedure takes place similarly in the case of a hyperopia correction. The cornea thickness must then be measured peripherally at the point of the maximum ablation; the formula specified in item 6 is then to be replaced appropriately.

The thickness and profile measurements on the eye as set forth above can be supplemented by determination of the refractive power distribution of the eye. In order to achieve this, the lens 162 in FIG. 7 is replaced by a lens array (not illustrated) with p×q lenses. The radiation coming from the radiation source 149 is thereby projected onto the eye in a fashion split into p×q component beams (not illustrated). The lens array can be moved up onto the eye or away from the latter. It is now brought into a position such that focusing takes place at least partially on the retina. A further beam splitter is now used at a location between the surface of the eye and the lens 170. If, now, the spatial distribution of the points of light on the retina deviates from the distribution of points generated by the lens array, the refractive power distribution or the image-forming property of the eye is not ideal, that is to say the eye does not form an optimal image of a plane wave front impinging on the cornea. This deviation (for example spherical aberration, coma, etc.) can then be displayed on a monitor.

Known tonometers (eye pressure measuring devices) have the disadvantage that they can measure the intraocular pressure only indirectly. The measurement is performed, for example, via a force which is necessary in order to flatten a corneal surface on a prescribed surface (applanation tonometer). The "flattened" force is, however, a function of the corneal thickness and the curvature of the cornea. The known tonometers proceed from a standardized normal corneal thickness and normal corneal curvature. In the case of a deviation of the cornea from the standard values, an intraocular pressure determined in such a way then does not correspond to the actual value. The thicker or the more strongly curved the cornea, the more strongly the internal pressure determined in a known way deviates upwards from the actual value. This can lead to the administration of unnecessary or even harmful medicaments for lowering eye pressure because of the supposedly excessively high eye pressure. However, this faulty measurement or misinterpretation can also have the effect, for example, of delaying the diagnosis of glaucoma.

It is now proposed to combine the device according to the invention with a tonometer. The ("wrong") intraocular pressure measured with a known tonometer is corrected computationally by using the corneal curvature and the corneal thickness determined with the device according to the invention. The correction can be performed by inputting the values into a computer, or automatically by electronically linking the two units.

The devices according to the invention, their design variants and their measuring instruments can be networked, it thereby being possible to undertake conditioning and storage of data even at remote locations and compare them with other data.

As already mentioned partly above, the device according to the invention serves the purpose of opthalmological measurement of the corneal thickness, the corneal thickness profile, the front and back corneal profiles;

the depth of the anterior chamber, the profile of the depth of the anterior chamber;

the lens thickness, the lens thickness profile, the front and back lens profiles, the vitreous humor depth, the vitreous humor profile;

the retinal layer thickness, the retinal surface profile;

the epithelial thickness, the epithelial profile, the front and back epithelial profile;

the corneal flap thickness, the flap thickness profile, the front and rear flap profiles, the flap position;

the corneal stroma thickness, the stroma profile, the front and rear stroma profiles, Further measurements can be undertaken during post-operative follow-up examinations after refractive surgery.

What is claimed is:

1. A method for measuring optical properties of at least two mutually spaced regions in a transparent and/or diffusive object within a measuring time of a sub-second range, using a Michelson-Interferometer and the object being irradiated with the aid of a number of measuring beams corresponding to the number of said regions, in each case said at least two measuring beams having a coherence-length that is shorter than a distance between said regions to be measured and said at least two measuring beams having an optical path mutual difference, except for a determination tolerance, said difference corresponds to a geometrical distance in the measuring beam direction between in each case two regions of said at least two regions, and each reflection beam of the measuring beams, which is reflected by one of said regions being superimposed in an interfering fashion with a third beam having a temporal variation in path length, and said interfering fashion being detected in relation to an actual path length of said temporal variation in path length.

2. A method according to claim 1, wherein at least two measuring beams having an optical path mutual difference being combined to form a single beam configuration with a single optical axis and being directed to said object for thickness measurement.

3. A method according to claim 1, wherein in each case at least two measuring beams run at a distance next to one another in order to determine a surface profile.

4. A method according to claim 1, wherein the measuring beams in each case have mutually differing radiation frequencies.

5. Device for measuring in a measuring time of sub-second range optical properties of at least two mutually spaced regions at a transparent and/or diffusive object, said device comprising:

a detector-unit, an optical arrangement having a Michelson interferometer, said interferometer having a measuring and a reference arm, said interferometer having a radiation source generating a radiation being emitted into said measuring and reference arm, into said measuring arm said optical object being introduced, said object having at least one reflecting region, said reference arm having a path length variation unit for said radiation in said reference arm and a reflector for reflecting said radiation, with the aid of said path-length-variation unit a periodic change in path length for the radiation in said reference arm being generated and reflected to said detector-unit, said measuring arm having a detour unit said detour-unit being arranged upstream of said object, said detour-unit creating at least one first and at least one second measuring beam, said detour-unit imparting said first measuring beam with a detour against said second measuring beam, said detour creating a longer optical way to said first measuring beam in relation to said second measuring beam, and except for a determination tolerance, said detour being selected is equal to the distance between said spaced regions to be measured, said radiation-source generating a radiation having a coherence-length that is shorter than the distance between said two regions to be measured;

said detector-unit detecting an interfering fashion of said reflected radiation of said reference arm with reflected radiation of said first and second measuring beam radiation in relation to an actual path-length of said reference arm.

6. Device according to claim 5, wherein the radiation of the source beam can be split at least into two different directions of polarization, and the detour unit has at least two beam splitters with the aid of which the second measuring beam, having a polarization different to that of the first measuring beam, can be guided via the detour.

7. Device according to claim 5, wherein the radiation source of the optical arrangement of the Michelson interferometer is designed in such a way that the radiation has at least two different radiation center wavelengths and the detour unit has at least two wavelength-selective beam splitters with the aid of which the second measuring beam, having an other radiation frequency different to that of the first measuring beam, can be guided via the detour.

8. Device according to claim 5, wherein in the detour unit the geometrical-optical length of the detour can be varied by adjusting the distance of a deflecting mirror with reference to one of the beam splitters.

9. Device according to claim 5, further comprising a memory unit in which it is possible to store path lengths of the path length variation unit, in the case of which path lengths it is possible to get an interference status of the first and third as well as of the second and third measuring radiation in order to determine a thickness value in the case of first and second measuring beams focused approximately on one axis.

10. Use of device for measuring in a measuring time of a sub-second range a thickness and/or distance of optical regions, present in a transparent and/or diffusive object, of different optical properties including reflective index transitions, said device comprising:

a detector-unit, an optical arrangement having a Michelson-Interferometer, said interferometer having a measuring and a reference arm, said interferometer having a radiation-source generating a radiation being emitted into said measuring and reference arm into said measuring arm said transparent and/or diffusive object being introduced, said object having at least one reflecting region, said reference arm having a path-length-variation-unit for said radiation in said reference arm and a reflector for reflecting said radiation as a third beam, with the aid of said path-length variation-unit a periodic change in path-length for said radiation in said reference arm being generated and reflected to said detector-unit, said measuring arm having a detour-unit, said detour-unit being arranged upstream of said object, said detour-unit creating at least one first and at least one second measuring beam, said detour-unit imparting said first measuring beam with a detour against said second measuring beam, said detour creating a longer optical way to said first measuring beam in relation to said second measuring beam, and except for a determination tolerance, said detour being selected is equal to the distance between said spaced regions in said transparent and/or diffusive object to be measured, said radiation-source generating a radiation having a coherence-length that is shorter than the distance between said two regions to be measured;

said detector-unit detecting an interfering fashion of said third beam with reflected radiation of said first and second measuring beam radiation in relation to an actual path-length of said reference arm, the thickness and/or the distance of the optical regions is determined by the interference fashion in relation to the length-value of the path-length-variation of the third beam and the detour-length-value of the detour-unit.

11. A method according to claim 1, wherein the third beam having a periodic variation in path length.

12. A method according to claim 2, wherein the single beam configuration is moved over the object.

13. A method according to claim 12, wherein the single beam configuration is moved periodically over the object.

14. Method according to claim 1, wherein the measuring beams in each case have mutually differing polarization states.

15. Method according to claim 1, wherein in each case at least one of said measuring beams is focused onto one of the regions.

16. Method according to claim 1, wherein a reference corresponding to a prescribed path length is defined in the case of the temporal path length variation in the third beam.

17. Device according to claim 8, wherein the beam-splitter and each deflecting-mirror assigned to the latter are aligned relative to one another in such a way that each deflected measuring beam with the non-deflected one has a single optical axis in the object.

18. Device according to claim 5, further comprising one focusing unit for each measuring beam, in order to be able to focus the latter onto one region each.

19. Device according to claim 5, further comprising a memory unit in which it is possible to store path-lengths of the path-length-variation-unit, in the case of which path-lengths it is possible to get an interference status of the first and third as well as of the second and third measuring radiation in order to determine a surface-profile in the case of laterally neighboring first and second beams.

20. Use of a device for measuring in a measuring time of a sub-second range a thickness and/or a distance of optical regions, present in a transparent and/or diffusive object of different optical properties, such as, for example reflective index transitions, where said object is difficult to be fixed in a timely stable position, said device comprising:

a detector-unit, an optical arrangement having a Michelson-Interferometer, said interferometer having a measuring and a reference arm, said interferometer having a radiation source generating a radiation being emitted into said measuring and reference arm into said measuring arm said transparent and/or diffusive object being introduced, said object having at least one reflecting region, said reference arm having a path-length-variation-unit for said radiation in said reference arm and a reflector for reflecting said radiation as a third beam, with the aid of said path-length-variation-unit a periodic change in path-length for said radiation in said reference arm being generated and reflected to said detector-unit, said measuring arm having a detour-unit, said detour-unit being arranged upstream of said object, said detour-unit creating at least one first and at least one second measuring beam, said detour-unit imparting said first measuring beam with a detour against said second measuring beam, said detour creating a longer optical way to said first measuring beam in relation to said second measuring beam, and except for a determination tolerance, said detour being selected is equal to the distance between said spaced regions in said transparent and/or diffusive object to be measured, said radiation-source generating a radiation having a coherence-length that is shorter than the distance between said two regions to be measured; said detector-unit detecting an interfering fashion of said third beam with reflected radiation of said first and second measuring beam radiation in relation to an actual path-length of said reference arm, the thickness and/or the distance of the optical regions is determined by the interference fashion in relation to the length value of the path-length-variation of the third beam and the detour-length value of the detour-unit.

21. Use of a device according to claim 20 wherein the object is the human eye.

22. Use of a device for measuring in a measuring time of a sub-second range a profile of an object, which reflects radiation and is difficult to be fixed in a timely stable position, said device comprising:

a detector-unit, an optical arrangement having a Michelson-Interferometer, said interferometer having a measuring and a reference arm, said interferometer having a radiation-source generating a radiation being emitted into said measuring and reference arm into said measuring arm said object being introduced, said object having at least one reflecting region, said reference arm having a path-length-variation-unit for said radiation in said reference arm and a reflector for reflecting said radiation as a third beam, with the aid of said path-length-variation-unit a periodic change in path-length for said radiation in said reference arm being generated and reflected to said detector-unit, said measuring arm having a detour-unit, said detour-unit being arranged upstream of said object, said detour-unit creating at least one first and at least one second measuring beam, said detour-unit imparting said first measuring beam with a detour against said second measuring beam, said detour creating a longer optical way to said first measuring beam in relation to said second measuring beam, and except for a determination tolerance, said detour being selected is equal to the difference of the profile level values between lateral level points on said object to be profiled, said radiation-source generating a radiation having a coherence-length that is shorter than the distance between said two regions to be measured;

said detector-unit detecting an interfering fashion of said third beam with reflected radiation of said first and second measuring beam radiation in relation to an actual path-length of said reference arm, the profile of the object being determined by the interference fashion in relation to the length-value of the path-length-variation of the third beam and the detour-length-value of the detour-unit and the values of the lateral level points.

23. Use of a device according to claim 22 wherein the object is the human eye.

* * * * *